United States Patent [19]

Watanuki et al.

[11] Patent Number: 5,266,897
[45] Date of Patent: Nov. 30, 1993

[54] MAGNETIC FIELD OBSERVATION WITH TUNNELING MICROSCOPY

[75] Inventors: Osaaki Watanuki, Kawasaki; Fuminori Sai, Yokohama; Kuniaki Sueoka, Kawasaki, all of Japan

[73] Assignee: International Business Machines Corporation, Armonk, N.Y.

[21] Appl. No.: 23,750

[22] Filed: Feb. 24, 1993

Related U.S. Application Data

[63] Continuation of Ser. No. 755,223, Sep. 5, 1991, abandoned.

[30] Foreign Application Priority Data

Sep. 5, 1990 [JP] Japan .................................. 2-233438

[51] Int. Cl.$^5$ ............................................ G01R 33/02
[52] U.S. Cl. ...................................... 324/244; 324/260
[58] Field of Search ............. 324/200, 226, 244, 260, 324/261, 262; 250/306

[56] References Cited

U.S. PATENT DOCUMENTS 4,861,990 8/1989 Coley ................................. 250/306

OTHER PUBLICATIONS

U. Durig et al., Physical Review Letters, vol. 57, pp. 2403-2406 (10 Nov. 1986).
Y. Martin and H. K. Wickramasinghe, Applied Physics Letters, vol. 50, pp. 1455-1457 (18 May 1987).
R. Allenspach et al., Z Phys. B—Condensed Matter, vol. 67, pp. 125-128 (1987).
M. A. Taubenblatt, IBM Technical Disclosure Bulletin, vol. 32, pp. 250-251 (Aug. 1989).
C. Schonenberger and S. F. Alvarado, Review of Scientific Instruments, vol. 60, pp. 3131-3134 (Oct. 1989).
P. C. D. Hobbs et al., Applied Physics Letters, vol. 55, pp. 2357-2359 (27 Nov. 1989).
"Magnetic Imaging By Fe-coated MFM Tip" extended abstracts (37th Spring Meeting 1990) The Japan Society of Applied Physics and Related Societies, 31a PA-9, part II p. 434 (Mar. 1990) (in Japanese) (no translation).
C. Schonenberger et al., Journal of Applied Physics, vol. 67, pp. 7278-7280 (15 Jun. 1990).

Primary Examiner—Walter E. Snow
Attorney, Agent, or Firm—J. David Ellett, Jr.; Robert M. Trepp

[57] ABSTRACT

Tunneling microscopy can be used to observe simultaneously the topography of a sample surface that is conductive and data related to the magnetic field near the surface. A tunneling microscope apparatus has a cantilever supporting a tip which has a magnetic moment. To use the apparatus according to a first preferred method, a magnetic field alternating at a predetermined frequency is produced by the sample near the sample surface to vibrate the tip by a magnetic interaction with the magnetic moment. To use the apparatus according to a second preferred method, the direction of the magnetic moment of the tip is switched at a predetermined frequency to vibrate the tip by creating an interaction between the magnetic moment and a magnetic field of the sample. For both preferred methods, the tip is maintained at a distance from the sample surface so as to permit a tunneling current to flow. A component of the predetermined frequency of the tunneling current is extracted to obtain a signal for observing the magnetic field.

28 Claims, 7 Drawing Sheets

MAGNETIC FIELD OBSERVATION WITH TUNNELING MICROSCOPY

This application is a continuation of application Ser. No. 07/755,223, filed Sep. 5, 1991, now abandoned.

FIELD OF THE INVENTION

The present invention broadly relates to an apparatus and a method for observing a magnetic field near a sample surface. As used herein, the term "observing" and the like includes the concept of measuring a physical variable and visually displaying the measured data, and the concept of measuring a physical variable without displaying the measured data visually. More specifically, the invention relates to a scanning tunneling microscope (STM) capable of observing the topography of the sample surface and data related to the magnetic field near the surface simultaneously.

BACKGROUND ART

The recording density of magnetic recording apparatuses has been improved recently. In investigating defects or other features of a magnetic-field-producing component of such an apparatus, it is desirable to observe its surface topography with nanometer-scale accuracy and to observe near the surface the magnetic field that is produced by the component. In investigating causes of an attribute of the magnetic field, it is most desirable to observe both simultaneously.

Martin et al. proposed magnetic force microscopes (MFMs) using the principle of atomic force microscopy in the following documents:

(1) Y. Martin and H. K. Wickramasinghe, "Magnetic imaging by force microscopy with 1000 resolution," Appl. Phys. Lett., 50 (20), pp. 1455-1457, May. 18, 1987.

(2) P. C. D. Hobbs, D. W. Abraham and H. K. Wickramasinghe, Magnetic force microscopy with 25 nm resolution," Appl. Phys. Lett., 55 (22), pp. 2357-2359, Nov. 27, 1989.

These conventional MFMs vibrate a cantilever supporting a tip made of a magnetic material near its resonant frequency, and optically observe shifts in vibration amplitude which occur when the tip detects a magnetic force, by using an interferometer or similar instrument. As data related to the magnetic field, the first and second derivatives of the magnetic field can be obtained. The same apparatus can be used to observe the topography of a surface of a sample by causing the tip to sense the atomic force acting between an atom at the end of the tip and an atom on the sample surface, instead of the magnetic force. Thus the apparatuses in both (1) and (2) above allow not only the magnetic force, but also the surface topography to be observed after being translated into the form of forces acting on the tip end. However, it is difficult to observe both the magnetic force and the topography simultaneously, since the effects of the two forces must be distinguished in the observed amplitude shift. In addition, it is troublesome to set the optics for optical observation of the cantilever amplitude.

In addition to the difficulties in adjustment and operation discussed above, MFMs are not yet commercially available. It would be desirable for an apparatus to allow a magnetic field to be observed by using scanning tunneling microscopy, since the scanning tunneling microscopes are commercially available and relatively easy to adjust and operate. The following documents discuss approaches in which an STM is used to observe both the topography of a surface and the force acting on a tip of the STM simultaneously:

(3) N. A. Taubenblatt, "Lateral Forces and topography using the scanning tunneling microscope and optical sensing of the tip position," IBM Technical Disclosure Bulletin, Vol. 32, No. 3A, pp. 250-251, August 1989.

(4) U. During, J. K. Gimezewski and D. W. Pohl, "Experimental observation of forces acting during scanning tunneling microscopy," Phys. Rev. Lett., Vol. 57, No. 19, pp. 2403-2406, November 1986.

The apparatus described in (3) above shares a problem with the MFMs discussed above in that changes in amplitude of the STM tip are sensed optically. Further, the apparatus described in (3) it is not suitable for observation of a magnetic field produced by a magnetic head because it can detect only a force vibrating the tip in a direction parallel to the sample surface. In the apparatus described in (4) above, as shown schematically in FIG. 9, a thin gold film sample 100 whose topography is to be measured is placed on the end of a flexible cantilever 102. The cantilever 102 is vibrated with a small amplitude of about 0.25 Å near its resonant frequency by thermal excitation, which vibration is sensed in form of a component of the frequency of a tunneling current. When a gradient of the van der Waals force is present and acts between the end of a tungsten STM tip 104 and the sample surface, the resonant frequency of the cantilever 102 varies. Data on the van der Waals force can thus be obtained by analyzing the tunneling current with a spectrum analyzer and detecting shifts in the resonant frequency. Data on the sample topography are obtained in the form of signals applied to the z-direction driving means for the tip while the distance between the tip 104 and the sample surface is kept constant, on the basis of the tunneling current from which high-frequency components are eliminated.

Figure 9:
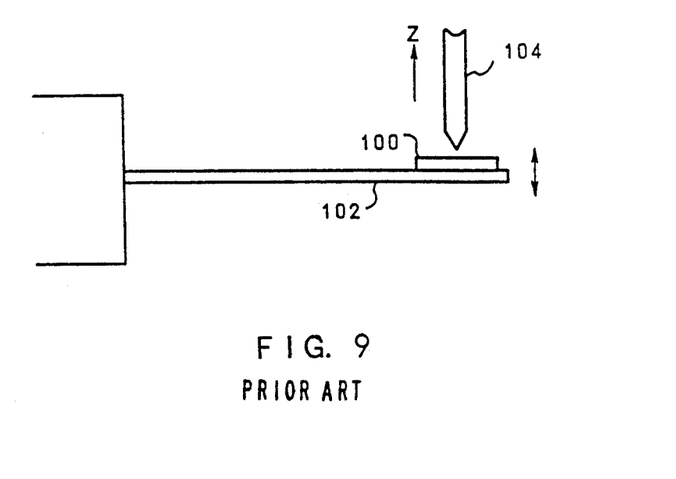
FIG. 9 is an explanatory view of a conventional prior-art apparatus using an STM for simultaneous observation of a sample topography and force.

However, even if the tip of the apparatus of FIG. 9 is made of a magnetic material, it is difficult to observe both the surface topography and the magnetic field of a sample when the sample is a thin-film magnetic head, for the following reasons:

(I) A magnetic head is usually attached to a slider. Further, it is coupled to a wire that supplies a current to produce a magnetic field. Therefore, the weight of a magnetic-head sample is typically much greater than that of a gold thin film. It is difficult to prepare a flexible cantilever that can support such a heavy sample.

(II) For a variation in the tunneling current caused by a force to be distinguished from one caused by the topography, the vibration frequency of the sample borne on the cantilever must be high. However, it is difficult to vibrate the cantilever at a high frequency while it is carrying a heavy sample such as a magnetic head. Even if it can be vibrated at high frequency, it would be difficult to detect a shift in the resonant frequency, because the vibration amplitude will be small.

(III) Since the sample and a sample carrier, which have much greater weight and volume than the tip, vibrate, the measurement is apt to be affected by noise, and the signal-to-noise (S/N) ratio of the measurement result is consequently decreased. In this instance noise can be air vibrations such as wind, sound waves, and the like, and/or insulator vibration.

In short, it is unnatural to move a sample that has a large volume and mass when the sample is to be observed with a small STM tip. There is accordingly a need for a measuring apparatus capable of obtaining data on both the topography and the magnetic field simultaneously, without moving the sample.

It is therefore an object of the invention to provide a novel apparatus capable of observing a magnetic field near a sample surface by means of a simple manipulation in an STM mode for measuring a tunneling current while scanning a tip across the sample surface.

A further object of the invention is to provide an apparatus and a method capable of simultaneously observing both the topography of a sample, even if the sample is heavy, and a magnetic field just above the surface, in an STM mode.

Another object of the invention is to allow observation of a magnetic field with a slightly modified conventional STM.

SUMMARY OF THE INVENTION

In one embodiment, the invention provides an apparatus for observing a magnetic field alternating at a predetermined frequency near a surface of a sample that is conductive in at least the surface. The apparatus comprises a cantilever and a tip supported by the cantilever. At least the end of the tip has a magnetic moment. The apparatus further comprises a voltage source for applying a voltage between the tip and the sample surface. The apparatus further includes a positioning mechanism for maintaining a distance between the tip and the sample surface such as to permit a tunneling current to flow. The apparatus of the present embodiment also comprises a signal detector electrically coupled to the tip for extracting a component of the predetermined frequency of a tunneling current caused by the interaction between the magnetic field and the magnetic moment.

Using the preferred embodiment of the apparatus described above, a magnetic field may be observed by producing a magnetic field alternating at a predetermined frequency to vibrate the tip by creating an interaction between the magnetic moment of the tip and the magnetic field while maintaining such a distance between the tip and the sample surface as to permit a tunneling current to flow. A component of the predetermined frequency of the tunneling current is extracted to obtain a signal for observing the field.

In a second preferred embodiment, the invention provides an apparatus for observing a magnetic field near a surface of a sample that is conductive in at least the surface. The apparatus comprises a cantilever and a tip supported by the cantilever. At least the surface of the end of the tip consists of a magnetic material. The apparatus also comprises a magnetic-moment-direction-switching mechanism for switching the direction of the magnetic moment of the tip at a predetermined frequency. The apparatus further comprises a voltage source for applying a voltage between the tip and the sample surface and a positioning mechanism for maintaining a distance between the tip and the sample surface such as to permit a tunneling current to flow. A signal detector electrically coupled to the tip is included in the apparatus for extracting a component of the predetermined frequency caused by the interaction between the magnetic field and the magnetic moment.

The second preferred apparatus of the invention may be used to observe a magnetic field by switching the direction of the magnetic moment of the tip at a predetermined frequency to vibrate the tip by creating an interaction between the magnetic moment and the magnetic field while maintaining such a distance between the tip and the sample surface as to permit a tunneling current to flow. A component of the predetermined frequency of the tunneling current is extracted to obtain a signal for observing the magnetic field.

In either embodiment of the invention, if the tip is scanned across the sample surface, the topography of the sample surface can be simultaneously observed by effectively removing high-frequency components of the tunneling current—by filtering, for example. The output of the z-direction control mechanism is continually adjusted so as to keep the tunneling current essentially constant after removal of the high-frequency components.

According to the invention, the magnetic field near a sample surface can be observed by means of a straightforward manipulation in an STM mode which measures the tunneling current while scanning the tip across the sample surface.

In addition, the invention provides simultaneous observation of the topography of a sample and the magnetic field immediately above the surface of the sample in an STM mode, even for a heavy sample.

Further, the invention permits observation of the magnetic field by using an apparatus that is a slightly modified version of a conventional STM.

PREFERRED AND BEST MODES FOR CARRYING OUT THE INVENTION

Figure 1:
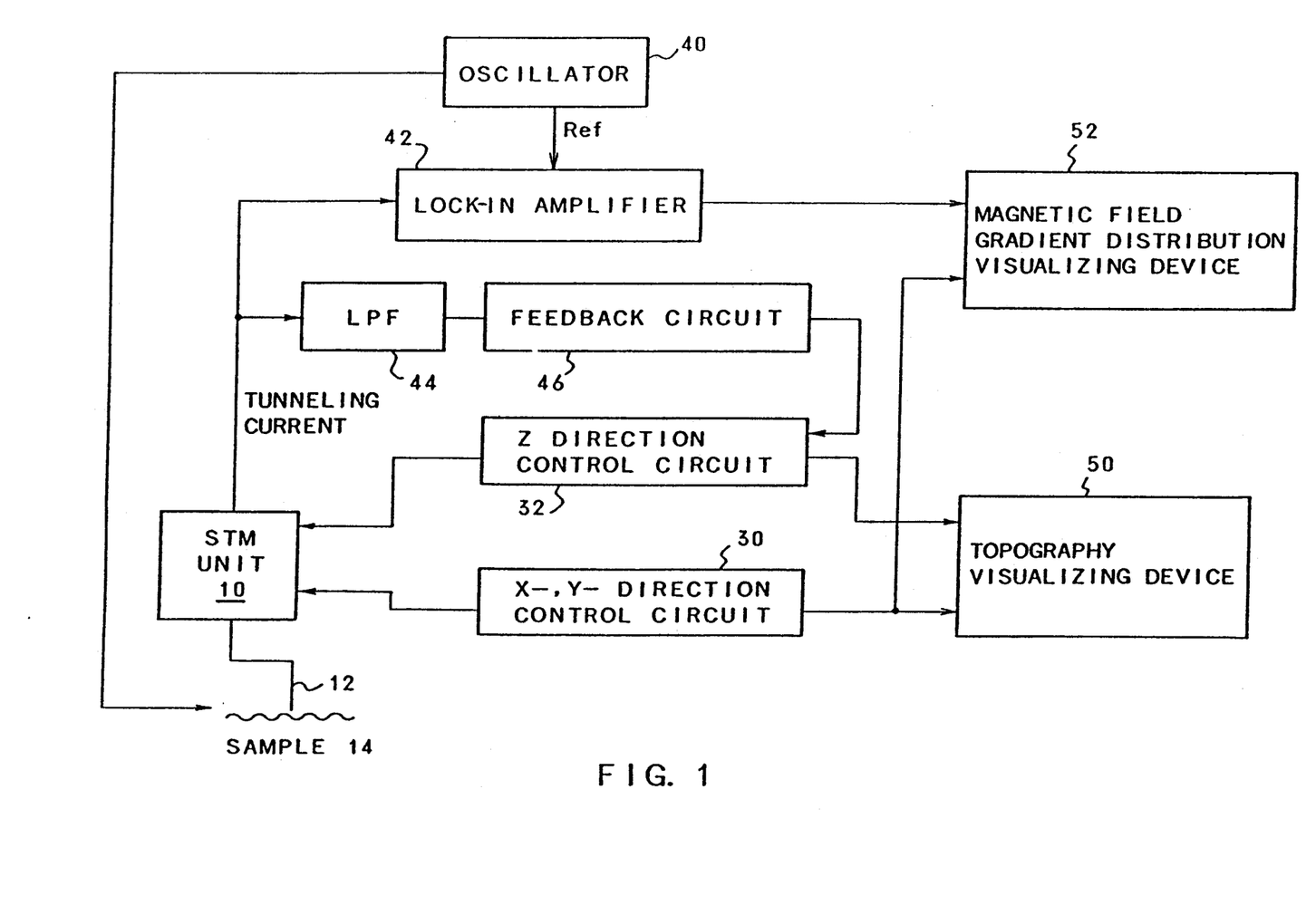
FIG. 1 is a block diagram showing a hardware arrangement embodying the invention.

Turning now to FIG. 1, an apparatus for simultaneously observing the topography of a sample 14, which is a thin-film magnetic head, and an alternating magnetic field produced near that head includes an STM unit 10 with a tip 12.

The STM unit of FIG. 1 is used to observe the topography of a conductive sample. To observe the surface of a non-conductive sample, a conductive material must be deposited thereon. Since a resolution of several hundred Å will be sufficient for investigation of a thin-film magnetic head, a Pt or other film with a thickness on the order of 100 to 200 Å may be uniformly sputter-coated over the surface.

A commercially available STM unit 10 can be used in the apparatus of FIG. 1 by replacing the original tip with a magnetic-field sensing tip by preparing a tip attached to a cantilever and having a magnetic moment in at least the end thereof.

Figure 2:
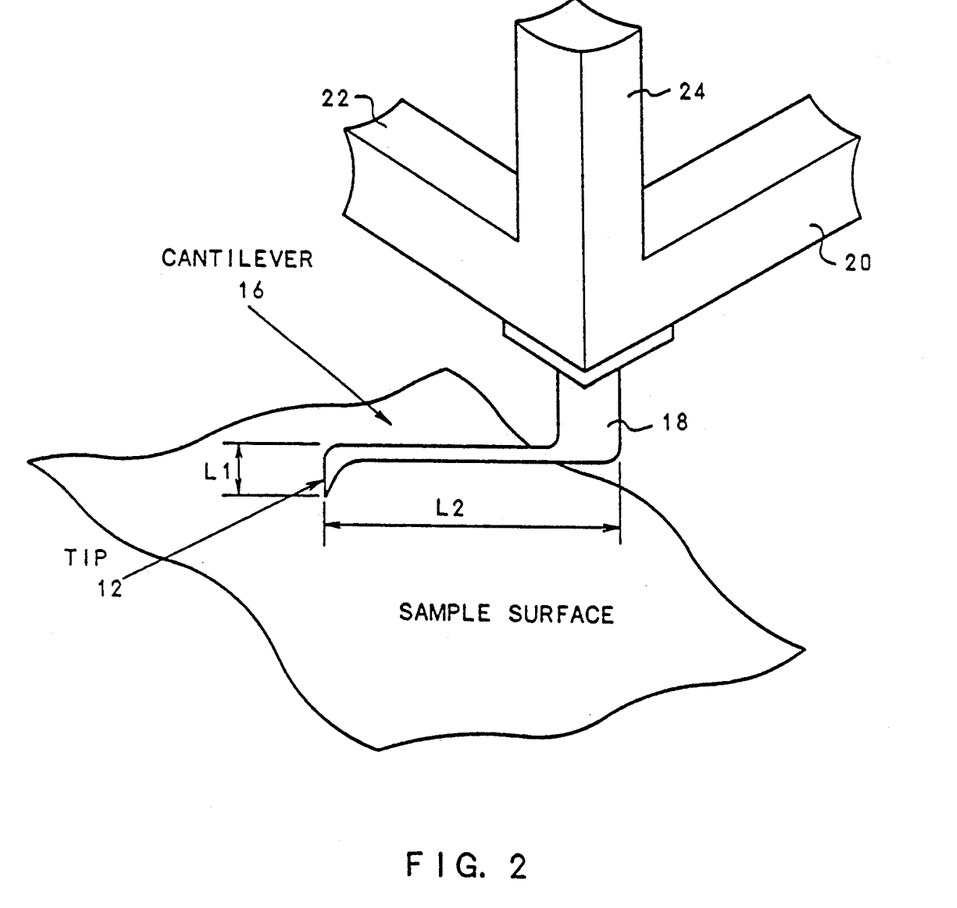
FIG. 2 is an enlarged view of a magnetic-field sensing tip.

FIG. 2 is an enlarged view of the tip 12 and its periphery. The tip 12 is provided at the free end of a cantilever 16 that extends in a direction parallel to the sample surface. In this example, the tip 12 has a radius of curvature of about 0.1 μm at its end, and its length L1 is from about 200 to about 300 μm. The cantilever 16, in the example, has a length L2 of about 700 μm and a diameter of about 100 μm. One end of the cantilever 16 is fixed to piezoelectric elements 20, 22 and 24 by a connection member 18 that extends in a z direction. The connection member 18, in this example, has a diameter of 250 μm. The members 16 and 18 may be formed in a single body. The piezoelectric elements 20, 22 and 24 are conventional STM piezoelectric elements that function as actuators for moving the cantilever 16 and hence the tip 12 in the x, y and z directions, respectively, to scan the sample surface while maintaining the tip at a distance from the sample surface such as to permit a tunneling current to flow. Here the x and y directions are essentially parallel to the sample surface, and the z direction is perpendicular to the same surface. The axial direction of the tip substantially coincides with the z direction.

At least the surface of the end of the tip 12 must be made of Fe, Ni, or another magnetic material. Alternatively, the entirety of the tip 12, including its interior, may be made of a ferromagnetic material. The tip 12 and the cantilever 16 may be made in a single body, or may be formed in separate elements and coupled together later.

When a magnet has the shape of a sharp needle, like the end of the STM tip, the magnetic moment is usually oriented in the axial direction of the needle owing to shape anistropy, and this direction is hardly affected by an external magnetic field. Therefore, an attractive or repulsive force in the z direction acts on the end of the tip 12 because of the magnetic field produced near the sample surface. Further, since the end of the tip 12 is brought within tens of angstroms of the sample surface, it is also affected by non-magnetic forces such as the van der Waals force. Therefore, the force $F_z$ in the z direction, which acts on the end of the tip 12, is expressed by the following equation (1):

$$F_z = F_n + m \frac{\partial H_z(r,t)}{\partial z}, \quad (1)$$

where $F_n$ represents non-magnetic forces such as the van der Waals force, m is the magnitude of the z component of the magnetic moment of the tip end, $H_z$ is the z component of a magnetic field H produced near the sample surface, r is the vector of the position, and t is the time.

The sum of these forces is applied to the cantilever 16 and deflects it. As a result, the end of the tip 12 is shifted in the z direction. The displacement is $\delta_z$ is determined by the following equation (2):

$$\delta_z = \frac{L^3 F_z}{3EI} = \frac{64}{3\pi}\left(\frac{L^3 F_z}{d^4 E}\right) = \frac{F_z}{k}, \quad (2)$$

where I is the moment of inertia, L is the arm length of the cantilever, E is the Young's modulus, and d is the spring constant of the cantilever.

According to the invention, since the distance between the tip and the sample surface varies not only with the roughness of the sample surface but also with the deflection of the cantilever by $\delta_z$, the tunneling current $J_T$ varies as expressed in the following equation (3):

$$J_T = J_o \exp(-A\phi^{\frac{1}{2}}(z+\delta_z)), \quad (3)$$

where z is the distance between the sample surface and the tip when there is no deflection of the cantilever, $\Phi$ is the work function (the work necessary for electrons to be detached from the sample surface), and $J_0$ and A are constants.

In FIG. 1, an x-and-y-direction control circuit 30 supplies piezoelectric elements for x-and-y-direction driving with voltage signals for scanning the tip 12 in the x and y directions. A z-direction control circuit 32 supplies a piezoelectric element for z direction driving with voltage signals for moving the tip 12 in the z direction. Specifically, these circuits may be transistor circuits that generate a high voltage on the order of 100 V.

In a typical STM, the tip is scanned in the x and y directions while the tunneling current is maintained at a constant level. Since the tunneling current increases when the tip moves above a protrusion in the sample surface, the tip is elevated to a position at which the current returns to the original level. In contrast, the tip is lowered at a depression in the surface. By repeating these operations and extracting and imaging the variation in the voltage applied to the piezoelectric element, it is possible to observe visually the surface structure on an atomic scale.

Observation of the topography by means of the invention is essentially based on the same principle. In the apparatus of the invention, however, the distance between the tip and the sample surface is not determined by the topography of the sample alone, but is also affected by forces applied to the tip end. Therefore, the tunneling current is determined by a combination of both effects. In order to measure the topography or the forces precisely, the two effects must be separated. For this purpose, the invention utilizes the fact that the magnetic field produced by a magnetic head is an alternating magnetic field.

Figure 3:
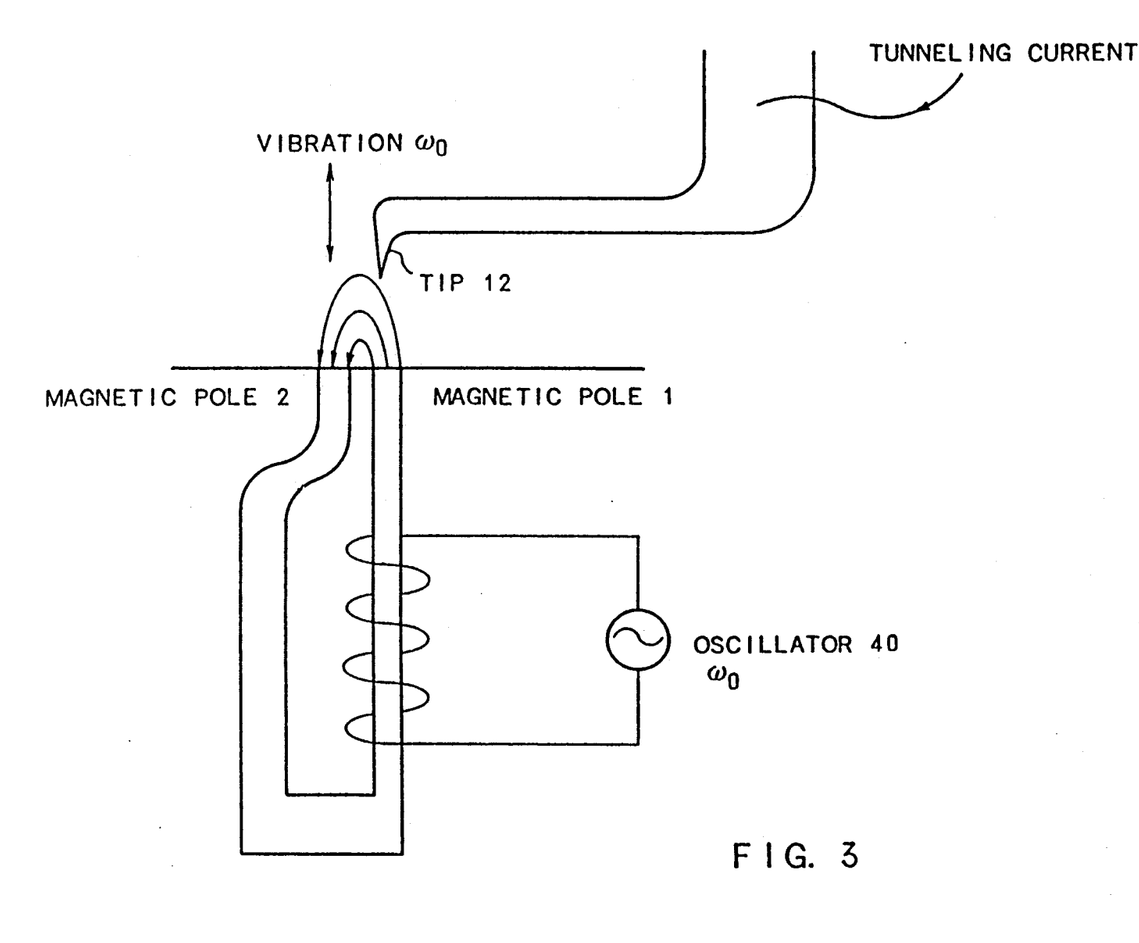
FIG. 3 is an explanatory view of the principle of magnetic field observation used in the foregoing embodiment.

The coil of the magnetic head 14 is supplied with an AC signal generated by an oscillator 40, as shown in FIG'S 1 and 3, and an alternating magnetic field is produced accordingly. The output of the oscillator 40 is also used as a reference signal (Ref) for a lock-in amplifier 42. Assuming here that the AC signal applied to the magnetic head is a sine wave of angular frequency $\omega_o$, the z component $H_z$ of the alternating magnetic field H produced by the magnetic head is expressed by the following equation (4):

$$H_z(r,t) = H_z(r) \cos \omega_o t. \quad (4)$$

under the influence of this alternating magnetic field, the deflection $\delta_z$ of the free end of the cantilever is expressed by the following equation (5):

$$\delta_z = \frac{1}{k}\left(f_n + m\frac{\partial H_z}{\partial z}\cos\omega_o\right), \quad (5)$$

where $H_z(r)$ is abbreviated as $H_z$. As is evident from the foregoing equation, the tip vibrates at an angular frequency $\omega_o$. Therefore, the tunneling current is modulated. From the modulated tunneling current the component of angular frequency $\omega_o$ is extracted through the lock-in amplifier 42.

The output f(J) of the lock-in amplifier 42 is expressed by the following equation (6):

$$f(J) \propto \exp\left(\frac{-A\Phi^{1/2}}{k} m \frac{\partial H_z}{\partial z}\cos\omega_o t\right). \quad (6)$$

Therefore, the logarithm of f(J) is proportional to the magnetic force $m\partial H_z/\partial z$, that is, the magnetic field gradient $\partial H_z/\partial z$.

Figure 4:
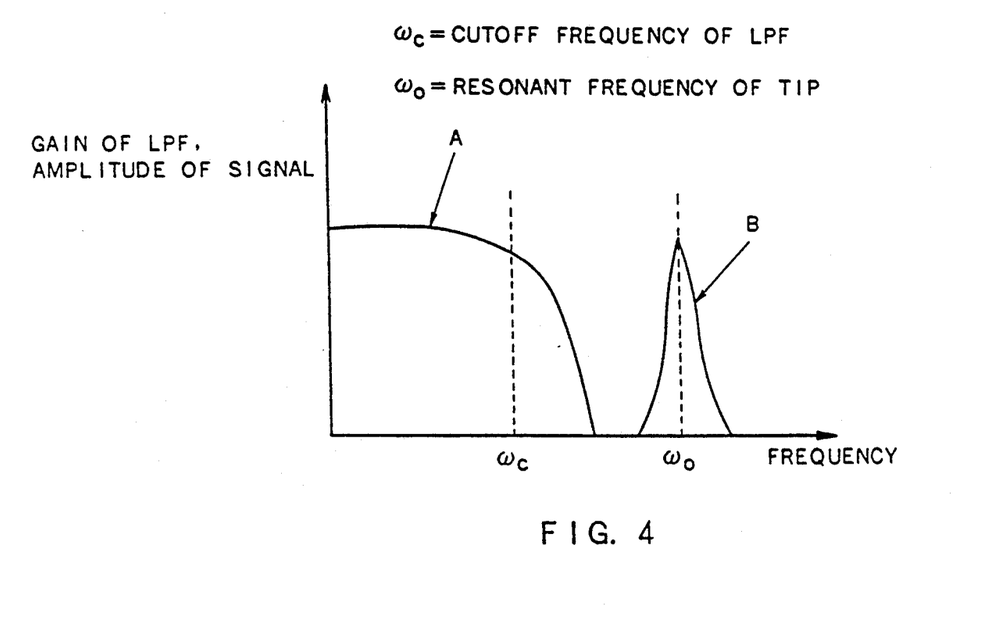
FIG. 4 is a diagram showing the frequency characteristic of the low-pass filter (LPF) used in the invention.

The magnitude of the magnetic field gradient $\partial H_z/\partial z$ is known from the amplitude of the component of angular frequency $\omega_o$ of the tunneling current extracted through the lock-in amplifier 42. On the other hand, the sign of the magnetic field gradient $\partial H_z/\partial z$ is known from the phase of the component of the angular frequency $\omega_o$ of the tunneling current. For example, if the sign of $\partial H_z/\partial z$ is plus near the magnetic pole in FIG. 3, the sign of the magnetic field gradient $\partial H_z/\partial z$ becomes minus near magnetic pole 2. This is known from the fact that the phase of the component of angular frequency $\omega_o$ of the tunneling current differs by 180 degrees near magnetic pole 1 and magnetic pole 2. This phase difference is detected by comparing the tunneling current with the reference signal (Ref) in the lock-in amplifier 42. As shown in FIG. 1, the tunneling current is also supplied to a low-pass filter (LPF) 44 in parallel connection with the lock-in amplifier 42. The output of the LPF 44 is supplied to a feedback circuit 46. As is shown in FIG. 4, the effect of the alternating magnetic field can be removed from the tunneling current by setting the cutoff frequency $\omega_o$ of the LPF 44 to a sufficiently low value relative to the frequency of the alternating magnetic field, that is, the peak $\omega_o$ of the AC components of the tunneling current. Since the frequency of an alternating magnetic field produced by thin-film magnetic head is usually set at from roughly 10 to roughly 20 kHz, it is easy to set such a cutoff frequency. The output of the LPF 44 is then essentially affected by the sample topography alone. The feedback circuit 46 compares the output of the LPF 44 with a reference value and, in order to eliminate the difference between them, supplies a feedback signal to the z-direction control circuit 32. The z-direction control circuit 32 supplies a voltage signal responsive to the feedback signal to the piezoelectric element for z-direction drive. As a result, the distance between the tip and the sample surface is maintained at an essentially constant level unaffected by the tip vibration.

Although the AC signal to be applied to the magnetic head is a sine wave in the foregoing example, it should be noted that, if a rectangular wave with a constant frequency is applied, the effect of the topography of the sample and the effect of the magnetic field can also be separated.

The topography is visualized by a topography visualizing device 50 according to the outputs from the x-and-y-direction control circuit 30 and the z-direction control circuit 32. Data related to the magnetic field, in this case the distribution of $\partial H_z/\partial z$, are visualized by a device for visualizing the magnetic field gradient distribution 52 according to the output of the lock-in amplifier 42 and the output of the x-and-y-direction control circuit 30. Examples of the topography visualizing device 50 and the magnetic field gradient distribution visualizing device 52 are computers, each of which includes a display screen. Note that the levels of the signals supplied from the x-and-y-direction control circuit 30 and the z-direction control circuit 32 to the STM unit 10 and the levels of the signals supplied from these circuits 30 and 32 to the visualizing devices 50 and 52 are required to be in a proportional relationship, but that the levels are not required to coincide.

Figure 5:
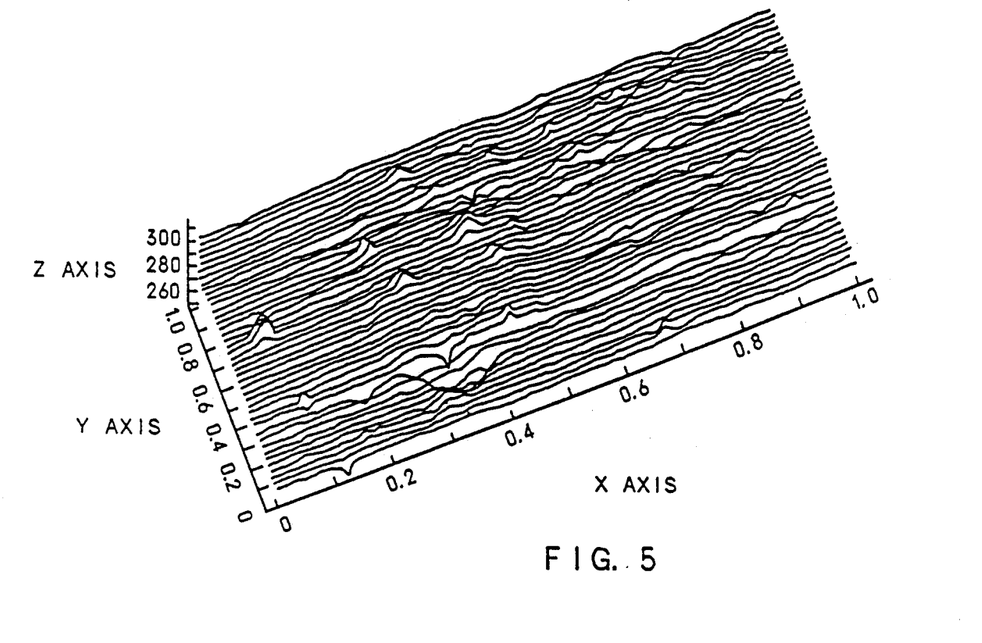
FIG. 5 is a graph showing an example of the result of observation of an area of sample topography.
Figure 6:
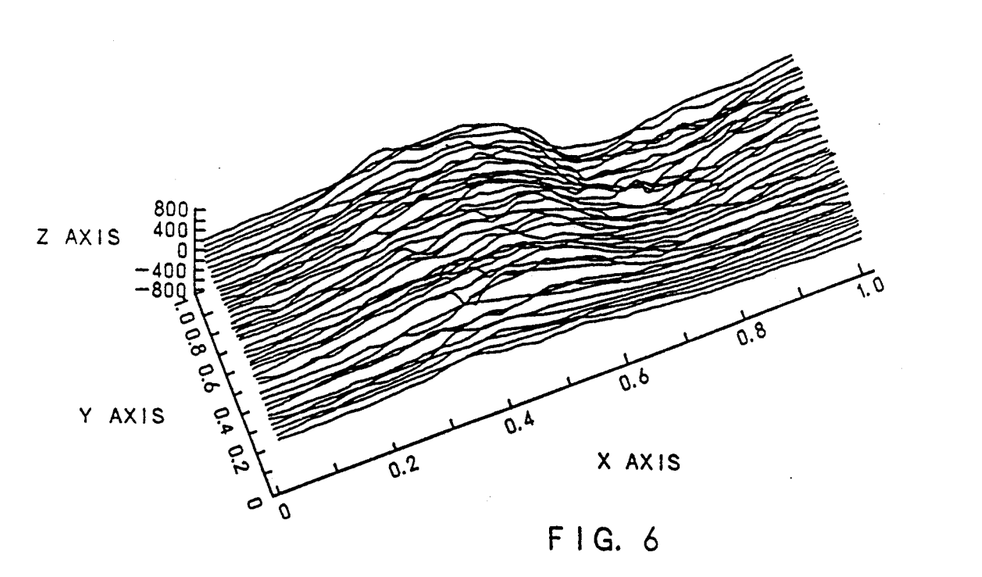
FIG. 6 is a graph showing the result of observation of the magnetic field corresponding to the area in FIG. 5.

FIG. 5 shows an output image of the topography of a side portion of a thin-film magnetic head. The x axis and the y axis correspond to the x-scanning direction and the y-scanning direction of the tip, respectively. The z-axis represents the height of the sample surface. The tip is scanned by about 8 μm in the x direction and by about about 2 μm in the y direction. Numerals on the graduations of each axis provide a relative scale in this example. FIG. 6 shows an output image of the magnetic field gradient distribution of the area shown in FIG. 5; the topography and magnetic field gradient distribution are measured simultaneously. Numerals on the graduations of the z axis represent the relative magnitudes of the magnetic field gradient.

Figure 7:
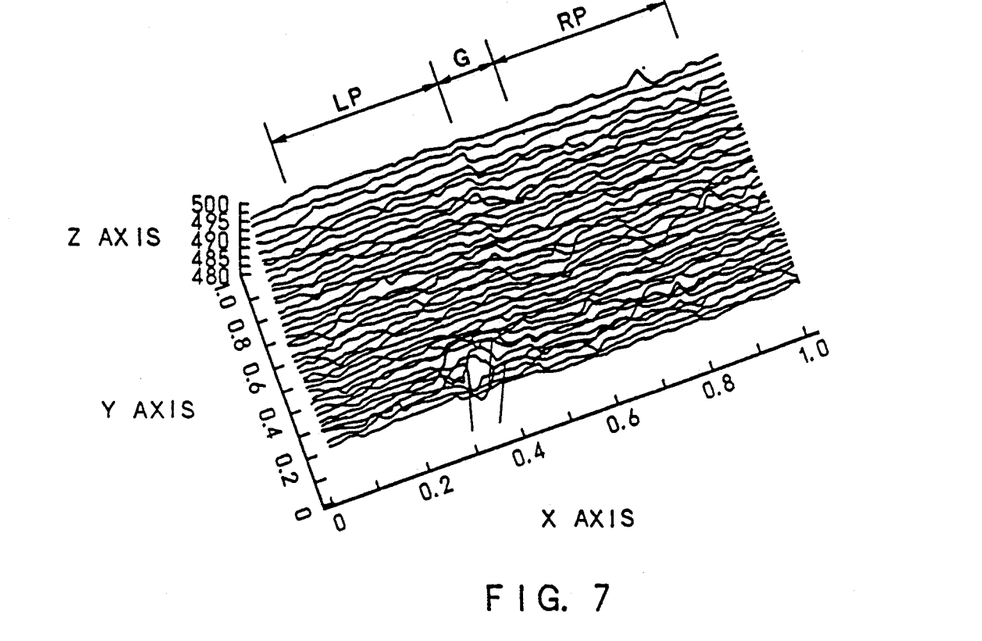
FIG. 7 is a graph showing a further example of the result of observation of an area of sample topography.
Figure 8:
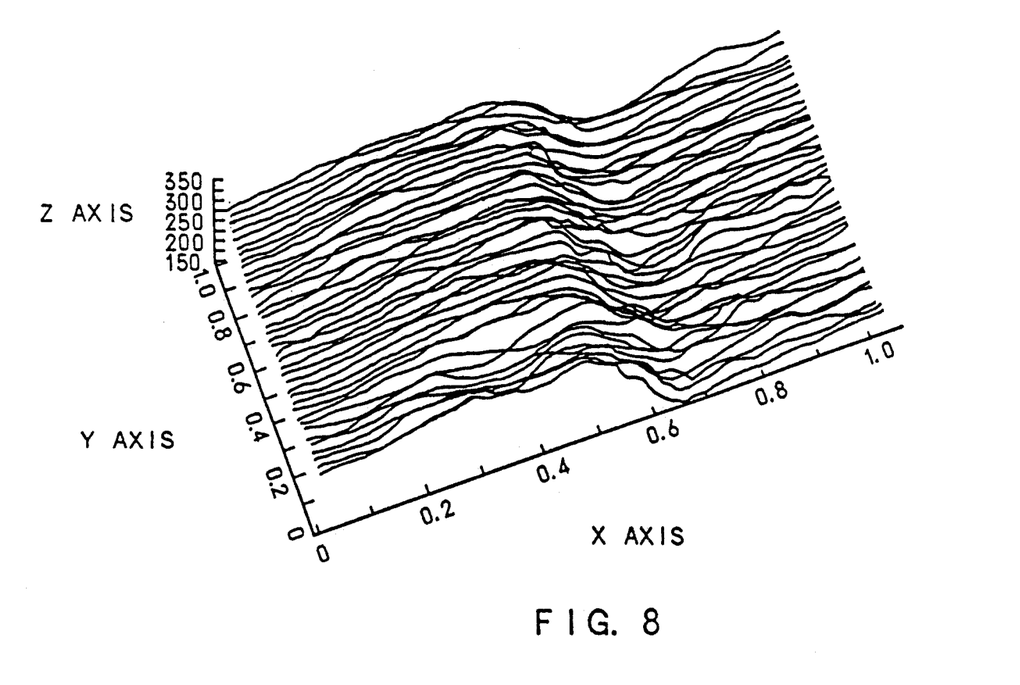
FIG. 8 is a graph showing the result of observation of the magnetic field corresponding to the area in FIG. 7.

FIG. 7 shows an output image of the topography at a central portion of the thin-film magnetic head. The size of the scanned area is the same as that shown in FIG. 5. Portion LP is the left magnetic pole, portion G is the gap, and portion RP is the right magnetic pole. A contaminating particle can be seen attached to the left magnetic pole. FIG. 8 shows an output image of the magnetic field gradient distribution of the area shown in FIG. 7; the topography and magnetic field gradient distribution are measured simultaneously. It is found that the value of the magnetic field gradient is low in the portion to which the contaminating particle is attached.

The previous example has provided observation of the dynamic magnetic field produced by a magnetic head. The invention can also be applied to observation of a static magnetic field such as that presented by a magnetic medium. The following example illustrates this kind of observation.

Figure 10:
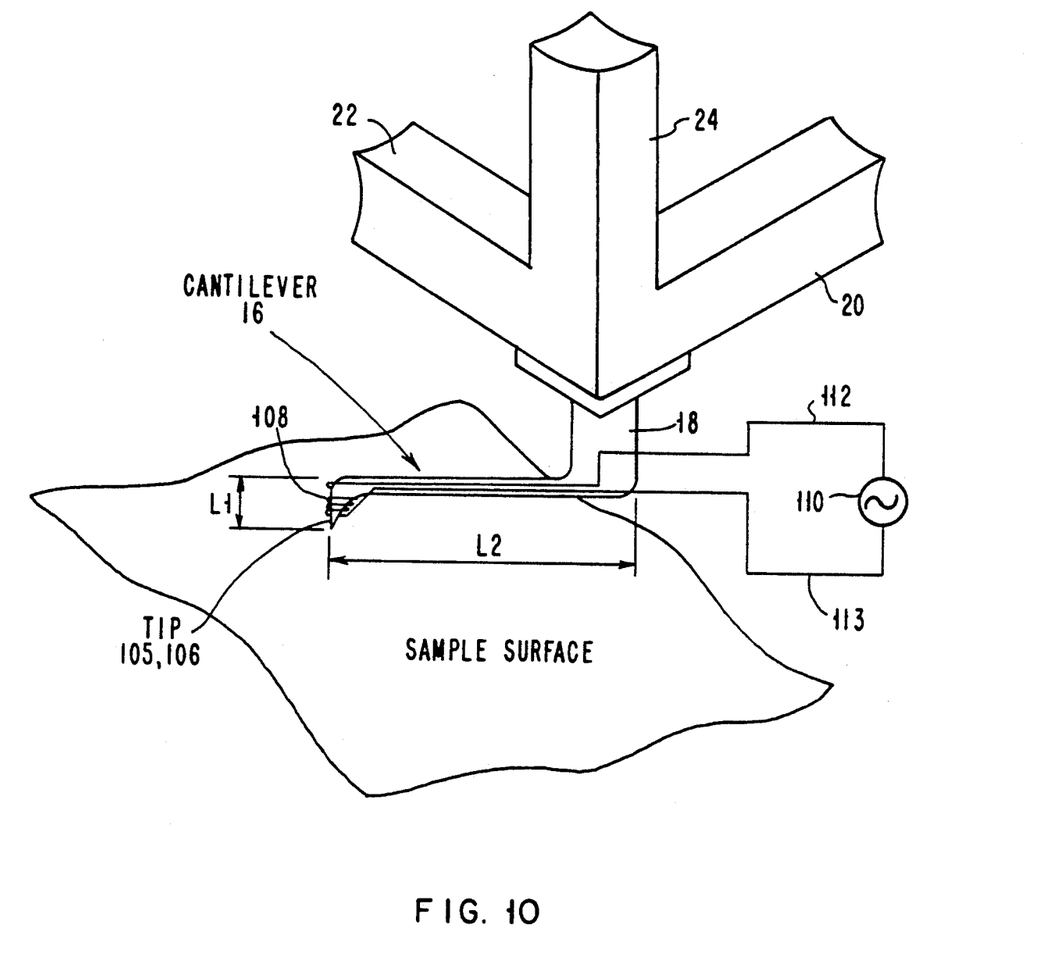
FIG. 10 is an alternative embodiment of the invention showing an enlarged view of a tip.

Referring to FIG. 10 an alternative embodiment of the invention is shown. In FIG. 10, like references are used for functions corresponding to the apparatus of FIG. 2. Whereas the tip end of tip 12 (shown in FIG. 2) of a dynamic field measuring apparatus is a magnet whose magnetic moment is fixed in one direction, the tip end 105 of tip 106 of a static magnetic measuring apparatus is configured so that the direction of its magnetic moment is switched at a predetermined frequency. Specifically, by winding a coil 108 around tip 106 and applying an AC signal of a predetermined frequency from an oscillator 110 coupled over leads 112 and 113 to coil 108, an alternating magnetic field is produced. The alternating magnetic field produces a magnetic moment at the end 105 of tip 106 at least and also switches the direction of the magnetic moment at the predetermined frequency. The AC signal may be either a sine wave or a rectangular wave. Therefore, in order to measure a static magnetic field, it is essential that the direction of the magnetic moment of the tip can be readily switched. An example of a tip structure satisfying this requirement is disclosed by Sueoka et al. in "Magnetic Imaging by Fe-coated MFM Tip," extended abstracts (37th Spring Meeting, 1990), The Japan Society of Applied Physics and Related Societies 31a PA-9, part II, p. 434, March 1990. According to this document, a tungsten tip body with a sputter-coated Fe thin film of 1000 to 2000 Å on its surface can be used.

As in the previous example, a magnetic force acts on the tip owing to the interaction between the magnetic moment and the magnetic field, and deflects the cantilever. Therefore, by extracting a component of the predetermined frequency from the tunneling current by means of the lock-in amplifier, the magnitude of the magnetic field gradient near the surface can be found. Further, the sign of the magnetic field gradient is known from the phase of the predetermined frequency component of the tunneling current. For example, in the case of a vertically magnetized film, if the sign of the magnetic field gradient is positive just above a magnetic domain in which the medium surface has N polarity, the sign of the magnetic field gradient will become negative just above a magnetic domain in which the medium surface has S polarity. This is known because the phase of the predetermined frequency component of the tunneling current detected by the lock-in amplifier differs by 180 degrees in the former and latter magnetic domains.

Considering that the magnetic field above the medium surface thus observed is tens of angstroms from the sample surface, it may be deemed that the magnetic domain pattern on the medium has been observed. However, for the successful observation of the magnetic domain pattern on the medium itself, the magnitude on the medium surface of the magnetic field produced by the magnetic moment of the tip end must be smaller than the magnetic coercive force Hc of the same medium. To satisfy the requirement, the number of turns of the coil and the current supplied to the coil must be set to appropriate values.

As in the previous example, by determining the output of the z-direction control circuit so that the tunneling current from which high-frequency components are effectively eliminated becomes constant, it is also possible to visualize the topography of the sample by using the outputs of the x-, y-, and z-direction control circuits.

The concept of switching the direction of the magnetic moment at the tip is also applicable to the observation of a dynamic field such as that produced by a magnetic head. If the tip 12 is magnetic only at its surface, the direction of the magnetic moment can be switched by means of an alternating field. In this case, the output of the lock-in amplifier 42 represents the absolute value of the magnitude of the field gradient. However, sign information is unobtainable if this approach is followed. The direction of the magnetic moment at the tip must be fixed, as in the first example, for sign information to be obtained.

It is not intended to limit the present invention to the specific embodiments described above. For example, the invention can also be used to observe the magnetic field at a particular point without scanning the tip. Although a primary object of visualization in the foregoing examples is the magnetic field gradient, it is also possible to process the gradient data and visualize the processed data such as the z component of the magnetic field or its second derivative. It is also possible to store the data in a storage device without visualizing them. It is recognized that these and other changes may be made in the embodiments specifically described herein without departing from the scope and teaching of the instant invention, and it is intended to encompass all other embodiments, alternatives, and modifications consistent with the invention.

We claim:

1. An apparatus for observing a magnetic field alternating at a predetermined frequency near a surface of a sample that is conductive in at least said surface, the sample being connected to an alternating-magnetic-field drive circuit adapted to drive the alternating magnetic field of the sample at the predetermined frequency, comprising:
   (a) a cantilever;
   (b) a tip supported by said cantilever, at least the end of said tip having a magnetic moment;
   (c) means for applying a voltage between said tip and said sample surface;
   (d) means for maintaining a distance between said tip and said sample surface such as to permit a tunneling current to flow; and
   (e) means electrically coupled to said tip for extracting a component of said predetermined frequency of tunneling current caused by the interaction between said magnetic field and said magnetic moment.

2. The apparatus according to claim 1 including means for visualizing data related to said magnetic field by using the output of said means (e).

3. The apparatus according to claim 1 wherein the end at least of said tip has a magnetic moment in the z direction, and said tip receives a force in the presence of a gradient in the z direction of a z component of the magnetic field, where the direction substantially perpendicular to said sample surface is defined to be the z direction.

4. An apparatus for simultaneously observing both the topography of a surface of a sample, which is conductive in at least said surface, and a magnetic field alternating at a predetermined frequency near the sample surface, comprising:
   (a) a cantilever;
   (b) a tip supported by said cantilever, at least the end of said tip having a magnetic moment;
   (c) means for applying a voltage between said tip and said sample surface;
   (d) alternating-magnetic-field drive means for driving the alternating magnetic field of the sample at the predetermined frequency;
   (e) x-direction driving means, y-direction driving means and z-direction driving means responsive to respective input signals for moving said tip in the x, y and z directions, where the x and y directions are defined to be substantially parallel to said sample surface, and the z direction is defined to be substantially perpendicular to said sample surface;
   (f) x-direction control means, y-direction control means, and z-direction control means for applying respective signals to said x-direction driving means, said y-direction driving means, and said z-direction driving means to scan said tip in the x and y directions while maintaining such a distance in the z direction between said tip and said sample surface as to permit a tunneling current to flow;
   (g) means electrically coupled to said tip and to said alternating-magnetic-field drive means for extracting a component of said predetermined frequency of a tunneling current caused by an interaction between said magnetic field and said magnetic moment;

(h) a low-pass filter electrically connected to said tip; and (i) means for determining the output of said z-direction control means so as to keep the output of said low-pass filter essentially constant.

5. The apparatus according to claim 4 including means for visualizing the topography of said sample surface by using outputs of said x-direction control means, said y-direction control means, and said z-direction control means.

6. The apparatus according to claim 4 including means for visualizing data related to said magnetic field by using outputs of said x-direction control means, said y-direction control means, and said means (f).

7. The apparatus according to claim 6 wherein the end at least of said tip has a magnetic moment in the z direction, and said tip receives a force in the presence of a gradient in the z direction of a z component of the magnetic field.

8. An apparatus for observing a magnetic field near a surface of a sample that is conductive in at least said surface, comprising:
(a) a cantilever;
(b) a tip supported by said cantilever, at least the surface of the end of said tip consisting of a magnetic material;
(c) means for switching the direction of the magnetic moment of said tip at a predetermined frequency;
(d) means for applying a voltage between said tip and said sample surface;
(e) means for maintaining a distance between said tip and said sample surface such as to permit a tunneling current to flow; and
(f) means electrically coupled to said tip for extracting a component of said predetermined frequency caused by the interaction between said magnetic field and said magnetic moment.

9. The apparatus according to claim 8 including means for visualizing data related to said magnetic field by using the output of said means (f).

10. The apparatus according to claim 9 wherein a magnetic moment in the z direction is produced at said tip, and said tip receives a force in the presence of a gradient in the z direction of a z component of the magnetic field, where the z direction is perpendicular to said sample surface.

11. An apparatus for simultaneously observing both the topography of a sample, which is conductive in at least said surface, and the magnetic field near the sample surface, comprising:
(a) a cantilever;
(b) a tip supported by said cantilever, at least the surface of the end of said tip consisting of a magnetic material;
(c) means for switching the direction of the magnetic moment of said tip at a predetermined frequency;
(d) means for applying a voltage between said tip and said sample surface;
(e) x-direction driving means, y-direction driving means, and z-direction driving means responsive to respective input signals for moving said tip in the x, y and z directions, where the x and y directions are defined to be substantially parallel to said sample surface, and the z is defined to be substantially perpendicular to said sample surface;
(f) x-direction control means, y-direction control means, and z-direction control means for applying respective signals to said x-direction driving means, said y-direction driving means, and said z-direction driving means to scan said tip in the x and y directions while maintaining a distance in the z direction between said tip and said sample surface such as to permit a tunneling current to flow;
(g) means electrically coupled to said tip for extracting a component of said predetermined frequency of a tunneling current caused by the interaction between said magnetic field and said magnetic moment;
(h) a low-pass filter electrically coupled to said tip; and
(i) means for determining the output of said z-direction control means so as to keep the output of said low-pass filter essentially constant.

12. The apparatus according to claim 11 including means for visualizing the topography of said sample surface according to the outputs of said x-direction control means, said y-direction control means, and said z-direction control means.

13. The apparatus according to claim 11 including means for visualizing data related to said magnetic field according to the outputs of said x-direction control means, said y-direction control means and said means (g).

14. The apparatus according to claim 13 wherein a magnetic moment in the z direction is produced at said tip, and said tip receives a force in the presence of a gradient in the z direction of a z component of the magnetic field.

15. A method for observing a magnetic field alternating at a predetermined frequency near a surface of a sample that is conductive in at least said surface, using a scanning tunneling microscope that includes a cantilever and a tip supported by said cantilever, the end at least of said tip having a magnetic moment, comprising the steps of:
(a) producing a magnetic field alternating at said predetermined frequency to vibrate said tip by creating an interaction between said magnetic moment and said magnetic field while maintaining a distance between said tip and said sample surface such as to permit a tunneling current to flow; and
(b) extracting a component of said predetermined frequency of said tunneling current, the component representing a measure of the magnetic field.

16. The method according to claim 15 including the step for visualizing data related to said magnetic field by using said predetermined frequency component of said tunneling current extracted in said step (b).

17. The method according to claim 16 wherein the end at least of said tip has a magnetic moment in the z direction, and said tip receives a force in the presence of a gradient in the z direction of a z component of the magnetic field in said step (a), where a direction substantially perpendicular to said sample surface is defined to be the z direction.

18. The method for simultaneously observing both the topography of a surface of a sample, which is conductive in at least said surface, and a magnetic field alternating at a predetermined frequency near the sample surface by using a scanning tunneling microscope that includes a cantilever; a tip supported by said cantilever, the end at least of said tip having a magnetic moment; x-direction driving means, y-direction driving means, and z-direction driving means responsive to respective input signals for moving said tip in the x, y, and z directions, where the x and y directions are defined to be substantially parallel to said sample and the z direction is defined to be substantially perpendicular to said sample surface; x-direction control means, y-direction control means, and z-direction control means for applying respective signals to said x-direction driving means, said y-direction driving means, and said z-direction driving means, comprising the steps of:
(a) producing a magnetic field alternating at said predetermined frequency to vibrate said tip by creating an interaction between said magnetic moment and said magnetic field, while scanning said tip along said sample surface and maintaining a distance between said tip and said sample surface such as to permit a tunneling current to flow to produce an alternating-magnetic-field-modulated scanned-surface-topography tunneling-current signal;
(b) extracting from said alternating-magnetic-field-modulated scanned-surface-topography tunneling-current signal an alternating-magnetic-field-modulation component of said predetermined frequency;
(c) eliminating from said alternating-magnetic-field-modulated scanned-surface-topography tunneling-current signal high-frequency components including said predetermined frequency to form a scanned-surface-topography tunneling-current signal component; and
(d) determining the output of said z-direction control means so as to keep the scanned-surface-topography tunneling-current signal component essentially constant after removal of high-frequency components.

19. The method according to claim 18 including a step for visualizing the topography of said sample surface by using the outputs of said x-direction control means, said y-direction control means, and said z-direction control means.

20. The method according to claim 19 including a step for visualizing data related to said magnetic field by using the outputs of said x-direction control means and said y-direction control means and said predetermined frequency component of said tunneling current extracted in said step (b).

21. The method according to claim 20 wherein the end at least of said tip has a magnetic moment in the z direction, and said tip receives a force in the presence of a gradient in the z direction of a z component of the magnetic field in said step (a).

22. A method of observing a magnetic field near a surface of a sample that is conductive in at least said surface by using a scanning tunneling micros includes a cantilever and a tip supported by said cantilever, at least the surface of the end of said tip consisting of a magnetic material, comprising the steps of:
(a) switching the direction of said magnetic moment of said tip at a predetermined frequency to vibrate said tip by creating interaction between said magnetic moment and said magnetic field while maintaining such a distance between said tip and said sample surface as to permit a tunneling current to flow; and
(b) extracting a component of said predetermined frequency of said tunneling current, the component representing a measure of the magnetic field.

23. The method according to claim 22 including a step of visualizing data related to said magnetic field by using said predetermined frequency component of said tunneling current extracted in said step (b).

24. The method according to claim 23 wherein, in said step (a), a magnetic moment in the z direction is produced at said tip, and said tip receives a force in the presence of a gradient in the z direction of a z component of the magnetic field, where the direction perpendicular to said sample surface is the z direction.

25. A method for simultaneously observing both the topography of a surface of a sample, which is conductive in at least said surface, and the magnetic field near the sample surface, using a scanning tunneling microscope that includes a cantilever; a tip supported by said cantilever, at least the surface of the end of said tip being made of a magnetic material; x-direction driving means, y-direction driving means, and z-direction driving means responsive to respective input signals for moving said tip in the x, y, and z directions, where the x and y directions are defined to be substantially parallel to said sample surface and the z direction is defined to be substantially perpendicular to said sample surface; and x-direction control means, y-direction control means, and z-direction control means for applying respective signals to said x-direction driving means, said y-direction driving means, and said z-direction driving means, comprising the steps of:
(a) switching the direction of the magnetic moment of said tip at a predetermined frequency and vibrating said tip by creating an interaction between said magnetic moment and said magnetic field while scanning said tip along said sample surface and maintaining a distance between said tip and said sample surface such as to permit a tunneling current to flow to produce a magnetic-interaction-modulated scanned surface topography tunneling-current signal;
(b) extracting from said magnetic-interaction-modulated scanned-surface-topography tunneling-current signal a magnetic-interaction modulation component of said predetermined frequency;
(c) effectively eliminating from said magnetic-interaction-modulated scanned-surface-topography tunneling-current signal high-frequency components including said predetermined frequency to form a scanned-surface-topography tunneling-current signal component; and
(d) determining the output of said z-direction control means so as to keep the scanned-surface-topography tunneling-current signal component essentially constant after removal of the high-frequency components.

26. The method according to claim 25 including a step for visualizing the topography of said sample surface, using outputs of said x-direction control means, said y-direction control means, and said z-direction control means.

27. The method according to claim 26 including the step of visualizing data related to said magnetic field by using the outputs of said x-direction control means and said y-direction control means and said predetermined frequency component of the tunneling current extracted in said step (b).

28. The method according to claim 27 wherein, in said step (a), a magnetic moment in the z-direction is produced at said tip, and said tip receives a force in the presence of a gradient in the z direction of a z component of the magnetic field.

* * * * *